United States Patent
Fujiwara et al.

(10) Patent No.: US 9,291,584 B2
(45) Date of Patent: Mar. 22, 2016

(54) METHOD OF STEEL GRADE DETERMINATION FOR STEEL MATERIAL

(75) Inventors: Kenji Fujiwara, Tokyo (JP); Hiroshi Kubota, Tokyo (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 267 days.

(21) Appl. No.: 13/981,965

(22) PCT Filed: Jan. 19, 2012

(86) PCT No.: PCT/JP2012/051043
§ 371 (c)(1),
(2), (4) Date: Oct. 3, 2013

(87) PCT Pub. No.: WO2012/105324
PCT Pub. Date: Aug. 9, 2012

(65) Prior Publication Data
US 2014/0016745 A1  Jan. 16, 2014

(30) Foreign Application Priority Data
Jan. 31, 2011  (JP) .................................. 2011-017787

(51) Int. Cl.
*G01N 23/223*  (2006.01)

(52) U.S. Cl.
CPC ........ *G01N 23/223* (2013.01); *G01N 2223/076* (2013.01)

(58) Field of Classification Search
CPC .......... G01N 23/223; G01N 2223/076; G01N 23/22; G21K 1/06; A61B 6/485
USPC ...................................................... 378/44, 45
See application file for complete search history.

(56) References Cited

U.S. PATENT DOCUMENTS

| 4,692,935 A | 9/1987 | Kumakura et al. |
| 5,325,416 A | 6/1994 | Saito et al. |
| 6,266,390 B1 | 7/2001 | Sommer, Jr. et al. |
| 2003/0194052 A1 | 10/2003 | Price et al. |
| 2010/0017020 A1* | 1/2010 | Hubbard-Nelson et al. .. 700/230 |

FOREIGN PATENT DOCUMENTS

| JP | 2000-338064 | 12/2000 |
| JP | 2007-275903 | 10/2007 |

OTHER PUBLICATIONS

Masanao Yoshida et al., "Fluorescent X-Ray . . . by SEA2001", Fukushima-Ken High Tech Plaza Shiken Kenkyu Hokoku, Nov. 21, 1996, pp. 181-182.

* cited by examiner

*Primary Examiner* — Jurie Yun
(74) *Attorney, Agent, or Firm* — Clark & Brody (57) ABSTRACT

The method of steel grade determination for a steel material having a substantially circular cross-section comprise: a detection step in which while a measurement section 2 including an irradiation section 21 for performing X-ray irradiation and a detection section 22 for detecting fluorescent X-rays is relatively moved along an outer peripheral surface of the steel material 4 with respect to the steel material for a predetermined time period necessary for analysis, the steel material is irradiated with X-rays from the irradiation section, and fluorescent X-rays radiated from the steel material are detected by the detection section; a calculation step of calculating a composition of the steel material based on fluorescent X-rays detected in the detection step; and a determination step of determining a steel grade of the steel material according to the composition calculated in the calculation step.

3 Claims, 5 Drawing Sheets

METHOD OF STEEL GRADE DETERMINATION FOR STEEL MATERIAL

TECHNICAL FIELD

The present invention relates to a method of steel grade determination for a steel material having a substantially circular cross-section, such as a pipe or a tube, and a bar. Particularly, it relates to a method of steel grade determination for a steel material having a substantially circular cross-section which allows steel grade determination to be easily and accurately performed. Hereinafter, "a pipe or a tube" is referred to as "a pipe" when deemed appropriate.

BACKGROUND ART

Until now, to determine the presence or absence of foreign materials (steel materials of a different steel grade) in a stage such as before the shipping of steel materials having a substantially circular cross-section, there have been cases where steel grade determination by use of a fluorescent X-ray analysis method is conducted. In such a fluorescent X-ray analysis method, analysis is conducted by irradiating any fixed position of a steel material with X-rays for a predetermined time period.

In steel grade determination of a steel material, while there is a method to conduct fluorescent X-ray analysis on the outer peripheral surface of the steel material, in the case of a steel material having a surface layer oxide scale on the outer peripheral surface, such method has a problem in that the variation of analysis values among analysis positions increases since there are some elements that are unevenly distributed in the surface layer oxide scale. In particular, since Cr, Cu, and Ni are unevenly distributed in a surface layer oxide scale, the variation of analysis values among analysis positions will increase in steel pipes containing not less than 0.3 mass % of any element of Cr, Cu and Ni.

When the determination on whether or not a steel material to be subjected to steel grade determination is of any steel grade (hereafter, referred to as an "arbitrary steel grade") is performed based on whether or not an analysis value of the steel material to be subjected to steel grade determination falls into a reference range which is predetermined in consideration of the composition range according to the manufacturing standard of the arbitrary steel grade and the variation of measurement; if the variation of analysis values among analysis positions is large, there is a risk that accurate steel grade determination cannot be performed since the analysis value may be out of the reference range of the arbitrary steel grade depending on analysis positions even if a steel material which is known in advance to be of the arbitrary steel grade is analyzed.

Figure 1:
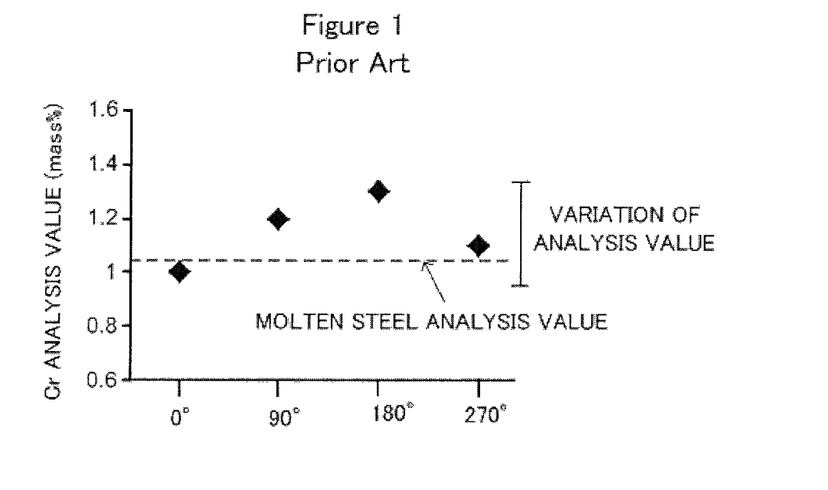
FIG. 1 is a diagram to show an example of analysis values of Cr when a fluorescent X-ray analysis of a steel pipe having a substantially circular cross-section is performed at four points in the pipe circumferential direction on the outer peripheral surface.

FIG. 1 is a diagram to show an example of analysis values of Cr when a fluorescent X-ray analysis of a steel pipe is performed at four points (positions of four directions of 0°, 90°, 180°, and 270° with assumption of the downward direction viewed from the pipe axis being 0°) in the pipe circumferential direction on the outer peripheral surface. While the analysis value of the molten steel of the steel material before casting is 1.04 mass %, the analysis values of the four points are 1.03 mass %, 1.18 mass %, 1.27 mass %, and 1.11 mass % showing a large variation.

On the other hand, when the surface oxide scale of this steel pipe is removed, it is confirmed that the variation of analysis values of Cr in the pipe circumferential direction is small. Therefore, the variation of the analysis values of Cr at four points in the pipe circumferential direction before removing the surface oxide scale is considered to be due to the surface oxide scale.

Accordingly, although it is conceivable to perform fluorescent X-ray analysis at multiple positions in the pipe circumferential direction and to use an average value of analysis values of respective positions to determine the steel grade of a steel material having a substantially circular cross-section, a problem exists in that it takes much time and effort to perform the fluorescent X-ray analysis at multiple positions.

Moreover, although a method is also conceivable in which the fluorescent X-ray analysis is performed after removing the surface oxide scale with a grinder etc. to eliminate the variation of analysis value due to the surface oxide scale, a problem also exists in that removing the surface oxide scale with a grinder requires time and effort.

Further, since a steel material having a substantially circular cross-section is subjected to end-face cutting for length adjustment and bevel processing after heat treatment, also conceivable is a method which performs fluorescent X-ray analysis on an end face of the steel material where there is no effect of surface oxide scale.

However, when fluorescent X-ray analysis is to be performed on an end face, the area which can be irradiated with fluorescent X-rays may become small depending on the diameter of steel material and the wall thickness of pipe when the steel material is a pipe, thereby making the analysis difficult.

Moreover, in a place where the steel material is transported in the longitudinal direction, it is difficult to install a fluorescent X-ray analyzer since if the fluorescent X-ray analyzer is installed in the transportation path of the steel material, there is a risk that the steel material collides with the fluorescent X-ray analyzer.

In particular, when fluorescent X-ray analysis is to be performed on an end face of the steel material in an automated manner in a manufacturing line, it is difficult to irradiate the end face of the steel material with fluorescent X-rays.

Further, as a method for determining a steel grade of a steel material, there is known a determination method described in Patent Literature 1; however, this determination method cannot solve the problem that steel grade determination cannot be performed easily and accurately in the fluorescent X-ray analysis of a steel material having a substantially circular cross-section.

CITATION LIST

Patent Literature

[Patent Literature 1] JP10-153594A

SUMMARY OF INVENTION

Technical Problem

The present invention has been made to solve such problems relating to prior arts and has an object to provide a method of steel grade determination for a steel material having a substantially circular cross-section, which allows steel grade determination to be easily and accurately performed.

Solution to Problem

Now, the principle of fluorescent X-ray analysis will be briefly described. In a fluorescent X-ray analysis, a substance to be analyzed is irradiated with X-rays and based on the fluorescent X-rays generated from the substance irradiated with X-rays, the composition of the substance is calculated. Here, description will be made on a case in which an energy dispersive type apparatus among fluorescent X-ray analyzers is used.

Figure 2:
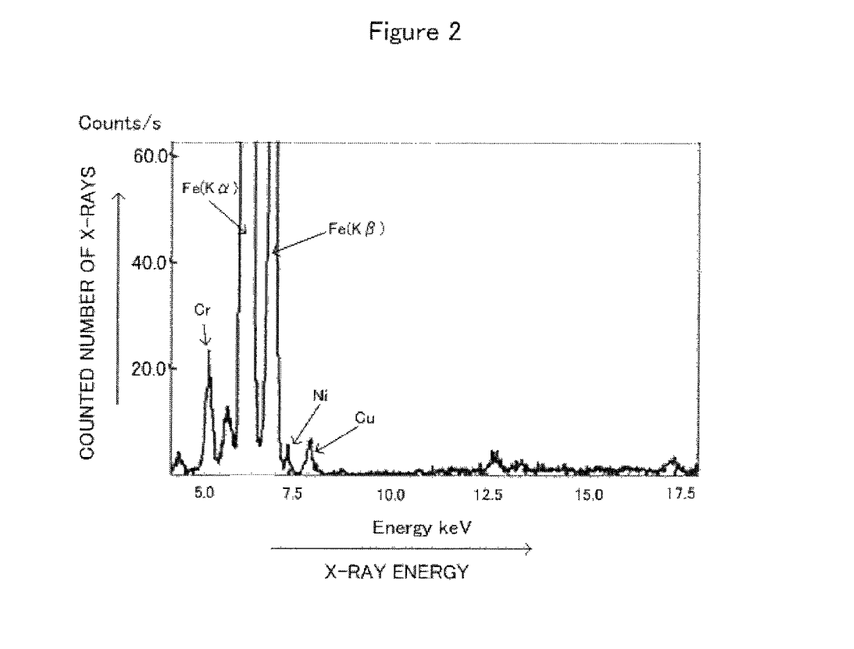
FIG. 2 is a diagram to show an example of energy spectrum of fluorescent X-ray obtained in fluorescent X-ray analysis of a steel material.

FIG. 2 is a diagram to show an example of energy spectrum of fluorescent X-ray obtained in fluorescent X-ray analysis of a steel material. The abscissa indicates the energy of fluorescent X-ray, and the ordinate represents the number of fluorescent X-ray counts at each energy level. Upon being irradiate with X-rays, each element radiates fluorescent X-rays having respective inherent energy.

In an energy spectrum, a peak occurs at the position of the energy level corresponding to each element, and its peak height (the number of X-rays counted) has a positive correlation with the concentration of each element in the steel material. To calculate a concentration from a peak height, a relationship between the concentration in a steel material and the peak height when X-ray irradiated is performed for a predetermined time period necessary for analysis is predetermined for each element, and a peak height when X-ray irradiation is performed for the predetermined time period necessary for analysis is inputted to the relationship to calculate a concentration. The relationship between the concentration and the peak height may be obtained by performing fluorescent X-ray analysis of a plurality of samples in which the concentration of each element is known. It is noted that since increasing the time for detecting fluorescent X-rays can decrease the effect of noise, the time period necessary for analysis is specified so as to decrease the effect of noise.

FIG. 2 shows a measurement example in a steel material added with Cr, Ni, and Cu, in which a peak of each element is observed.

Moreover, in a fluorescent X-ray analysis, it is general that the X-ray irradiation position is fixed during the time period necessary for analysis to accurately perform analysis at the X-ray irradiation position. Moreover, in an analysis in which an analysis value at a fixed point represents the composition of the entire target, in other words, in an analysis of a measurement object in which uneven distribution of each element is small, there is no need of moving the irradiation position during the time period necessary for analysis.

On the other hand, in a steel material having a substantially circular cross-section, when a measurement section including a function of X-ray irradiation and a function of fluorescent X-ray detection is relatively moved with respect to the steel material along the outer peripheral surface of the steel material, it is considered that the distance between the outer peripheral surface of the steel material and the measurement section (hereafter, referred to as a liftoff) varies such as when the roundness of the steel material is low or the steel material is curved, and a larger liftoff will decrease the amount of detectable fluorescent X-rays causing a variation of analysis value. Therefore, there has been no case that fluorescent X-ray analysis is performed while the measurement section is relatively moved with respect to the steel material during the time period necessary for analysis.

However, having investigated the variation of analysis values when the liftoff varied within a range of liftoff that occurs when the measurement section is relatively moved along the outer peripheral surface of the steel material with respect to the steel material, the present inventors have obtained a finding that such variation is smaller than that due to surface oxide scale. Moreover, they have obtained a finding that even if a fluorescent X-ray analysis is performed while the measurement section is relatively moved along the outer peripheral surface of a steel material for the time period necessary for analysis, the counting of fluorescent X-rays of each energy level is performed and the concentration can be calculated from its peak height as in the case in which the fluorescent X-ray analysis is performed with the X-ray irradiation position being fixed.

Figure 3:
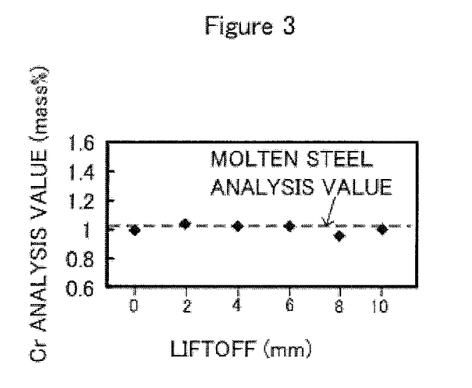
FIG. 3 is a diagram to show the relationship between the liftoff and the analysis value of Cr in a steel pipe.

FIG. 3 is a diagram to show the relationship between the liftoff and the analysis value of Cr in a steel pipe. While the liftoff is not more than 10 mm, the values of fluorescent X-ray analysis are 1.01 mass %, 1.04 mass %, 1.03 mass %, 1.03 mass %, 0.97 mass %, and 1.01 mass % with respect to the analysis value of molten steel of 1.04 mass %. It is found that the variation is far smaller than the variation of analysis value due to the surface oxide scale shown in FIG. 1. It is noted that the liftoff when the measurement section is relatively moved along the outer peripheral surface of the steel pipe is within 10 mm.

The present invention has been completed based on the above described finding by the present inventors. More specifically, in order to achieve the problem, the present invention provides a method of steel grade determination for a steel material having a substantially circular cross-section by means of a fluorescent X-ray analysis method, the method of steel grade determination for a steel material having a substantially circular cross-section comprising: a detection step in which while a measurement section including an irradiation section for performing X-ray irradiation and a detection section for detecting fluorescent X-rays is relatively moved along an outer peripheral surface of the steel material with respect to the steel material for a predetermined time period necessary for analysis, the steel material is irradiated with X-rays from the irradiation section, and fluorescent X-rays radiated from the steel material are detected by the detection section; a calculation step of calculating a composition of the steel material based on fluorescent X-rays detected in the detection step; and a determination step of determining a steel grade of the steel material according to the composition calculated in the calculation step.

In the calculation step of the present invention, calculating the composition of the steel material based on the detected fluorescent X-rays is, in other words, calculating the composition of the steel material based on the energy spectrum of fluorescent X-rays obtained from the result of fluorescent X-ray analysis of the steel material. Specifically, as in the method described above, the kind of element is identified based on the energy level of a peak position in the energy spectrum, and the concentration of the element is calculated from the peak height. It is noted that composition refers to the kind of elements constituting a steel material, and the concentration of each element.

Moreover, a steel grade is a category divided by the composition of steel material, and a composition range is determined for each steel grade. A steel material is classified into any one of steel grades by its composition.

Furthermore, the steel grade determination for a steel material is to determine to which steel grade the targeted steel material belongs, or to determine whether the targeted steel material is a steel material of a predetermined steel grade, or a steel material other than the predetermined steel grade.

Further, the determination step also includes calculating the composition of a steel material, without determining the steel grade of the steel material.

According to the present invention, since the steel material is irradiated with X-rays and fluorescent X-rays radiated from the steel material are detected while the measurement section is relatively moved along the outer peripheral surface of the steel material with respect to the steel material, the composition of the portion irradiated with X-rays is calculated in an averaged manner. Thus, the variation of analysis value is decreased, thereby allowing accurate steel grade determination to be performed.

Moreover, since a fluorescent X-ray analyzer which is the same as conventional ones can be used for the fluorescent X-ray analyzer in the present invention, and the time period necessary for analysis may also be the same as those in the past, steel grade determination can be easily performed.

That is, according to the present invention, even though it is possible to arrange for that the same equipment as in conventional fluorescent X-ray analysis is used, and the time period necessary for analysis is the same as in the past, the effect due to surface oxide scale can be reduced, thereby allowing accurate analysis to be easily performed. This analysis allows the steel grade determination of steel material having a substantially circular cross-section to be accurately and easily performed.

Moreover, since the fluorescent X-ray analysis is performed not on an end face, but on an outer peripheral surface of the steel material, it is easier to automate the fluorescent X-ray analysis in the manufacturing line.

Although the above described method allows accurate steel grade determination to be performed, in the case of a high alloy steel such as a steel material including Cr and Ni in which not less than 9 mass % of Cr is contained, a large variation may occur in the analysis values of Cr and Ni among steel materials even if they are of the same steel grade, and thus may cause an erroneous steel grade determination. This is because the generation condition of surface oxide scale may differ according to steel materials even in the same steel grade, and thereby the variation in the analysis values of Cr and Ni occur among steel materials. Then, the present inventors have studied the variation of the analysis values of Cr and Ni to obtain a finding that Cr and Ni are unevenly distributed in the surface oxide scale in a similar fashion, and in a place where there is much Cr, there is much Ni. Then, the variation of the ratio between Cr and Ni among steel materials is studied to obtain a finding that the variation of the ratio between Cr and Ni is smaller than the variations in the analysis values of Cr and Ni. Accordingly, based on this finding, the present inventors have found a method of performing steel grade determination according to the ratio between Cr and Ni.

Therefore, in the above described method of steel grade determination for a steel material having a substantially circular cross-section, it is preferable that the steel material contains Cr and Ni, and in the determination step, a steel grade of the steel material is determined according to the composition and according to a ratio between Cr and Ni concentrations in the composition.

According to such a preferred method, since the steel grade determination of a steel material is performed according to not only the composition but also the ratio between Cr and Ni concentrations, it is possible to perform the determination at a further higher accuracy.

Advantageous Effects of Invention

According to the present invention, it is possible to easily and accurately perform the steel grade determination of a steel material having a substantially circular cross-section.

BRIEF DESCRIPTION OF DRAWINGS

FIG. 5 is a schematic diagram to show a state in which a peak height increases while the measurement section 2 is relatively moved in the pipe circumferential direction and fluorescent X-rays are detected in the detection step and the calculation step.

FIG. 8 is a diagram to show results of analysis of a steel pipe in a manufacturing line by the fluorescent X-ray analysis relating to the first embodiment.

DESCRIPTION OF EMBODIMENTS (First Embodiment)

Figure 4:
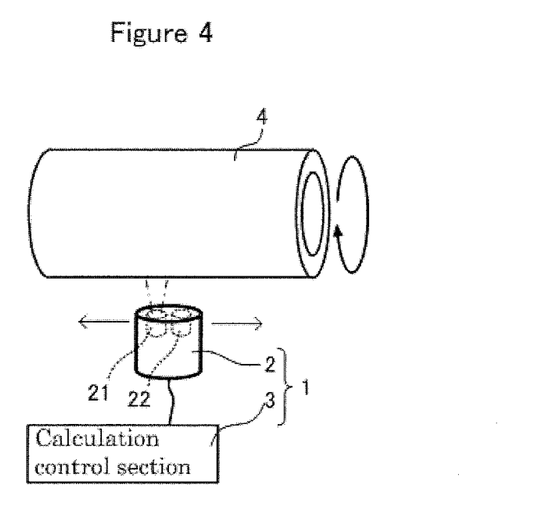
FIG. 4 is a schematic view to show an example of the method for determining the steel grade of a steel materials having a substantially circular cross-section relating to a first embodiment.

Hereafter, appropriately referring to the appended drawings, a method for determining a steel grade of a steel material having a substantially circular cross-section relating to a first embodiment of the present invention will be described. FIG. 4 is a schematic view to show an example of the method for determining a steel grade of a steel material having a substantially circular cross-section.

Although, in the present embodiment, description will be made taking an example in which the steel material having a substantially circular cross-section is a pipe, the steel material may be a bar.

A fluorescent X-ray analyzer 1 is, for example, of an energy dispersive type, and includes: a measurement section 2 having an irradiation section 21 for performing X-ray irradiation, and a detection section 22 for detecting fluorescent X-rays and transmitting an electric signal corresponding to the fluorescent X-rays; and a calculation control section 3 for controlling the operation of the measurement section 2 and receiving an electrical signal from the detection section 22 to calculate the composition.

A steel pipe 4 is placed on a rotary driving section (not shown) and rotated in the circumferential direction of the steel pipe 4 by the rotary driving section. The measurement section 2 is moved in the pipe axis direction of the steel pipe 4 by a linear driving section (not shown).

Therefore, the measurement section 2 is relatively moved along the outer peripheral surface of the steel pipe 4 by the rotary driving section and the linear driving section with respect to the steel pipe 4.

To perform steel grade determination of the steel pipe 4, firstly, the steel pipe 4 is irradiated with X-rays from the irradiation section 21 for a time period necessary for analysis, and fluorescent X-rays radiated from the steel pipe 4 are detected by the detection section 22 while the measurement section 2 is relatively moved along the outer peripheral surface of the steel pipe 4 with respect to the steel pipe 4, for example, by rotating the steel pipe 4 with the rotary driving section (detection step).

Next, the calculation control section 3 calculates the composition of the steel pipe 4 based on the fluorescent X-rays detected by the detection section 22 (calculation step).

Calculating the composition of the steel pipe 4 based on the detected fluorescent X-rays is, in other words, calculating the composition of the steel pipe 4 based on the energy spectrum of fluorescent X-rays obtained from the result of fluorescent X-ray analysis of the steel pipe 4. Specifically, as in the method described above, the kind of element is identified based on the energy level of a peak position in the energy spectrum, and the concentration of the element is calculated from the peak height.

The time period necessary for analysis is the same as in the case where fluorescent X-ray analysis is performed with the X-ray irradiation position being fixed in the fluorescent X-ray analyzer 1, and is for example 10 seconds in the present embodiment.

Since an average value of compositions of the positions irradiated with X-rays during the time period necessary for analysis is calculated, it is preferable that the measurement section 2 is relatively moved in a longer distance within a range in which the fluorescent X-ray analysis can be performed. When the measurement section 2 is relatively moved in the pipe circumferential direction, the distance of the relative movement is preferably not less than ½ round around the pipe so that the variation of analysis values among analysis positions is decreased. Moreover, since there is a risk that the variation of analysis value due to liftoff increases as the distance of the relative movement in the pipe circumferential direction increases, the distance of the relative movement is preferably not more than 2 rounds around the pipe. Furthermore, the distance of the relative movement of the measurement section 2 in the pipe circumferential direction is preferably one round so that an average value of compositions over the entire circumferential direction of the steel pipe 4 is calculated and that the variation of analysis value due to liftoff is decreased.

When the measurement section 2 is moved in the pipe axial direction, the distance of the relative movement is preferably not less than ½ of the pipe length so that the variation of analysis values among analysis positions is decreased. Moreover, since there is a large liftoff in the range of 200 mm from a pipe end, the upper limit of the distance of the relative movement is preferably a distance of the total length of the pipe subtracted by a length of 200 mm from both pipe ends.

It is noted that the relative movement may be performed both in the pipe circumferential direction and the pipe axis direction at the same time. Moreover, in the present embodiment, the measurement section 2 is relatively moved by one round in the pipe circumferential direction at a speed of 300 mm/sec during the time period necessary for analysis.

FIG. 5 is a schematic diagram to show a state in which a peak height increases while the measurement section 2 is relatively moved in the pipe circumferential direction and fluorescent X-rays are detected in the detection step and the calculation step.

It is supposed that the concentration of Cr, with the downward direction viewed from the pipe axis being 0°, is the same concentration in each of ¼ rounds: from an angle of 0° to less than 90°, from 90° to less than 180°, from 180° to less than 270°, and from 270° to less than 360°, and that the concentration is a low concentration in the range from 0° to less than 90°, a medium concentration in the ranges from 90° to less than 180°, and from 270° to less than 360°, and a high concentration in the range from 180° to less than 270°.

The measurement section 2 is relatively moved by one round in the pipe circumferential direction from the position of 0° during the time period necessary for analysis to perform fluorescent X-ray analysis.

Figure 5A:
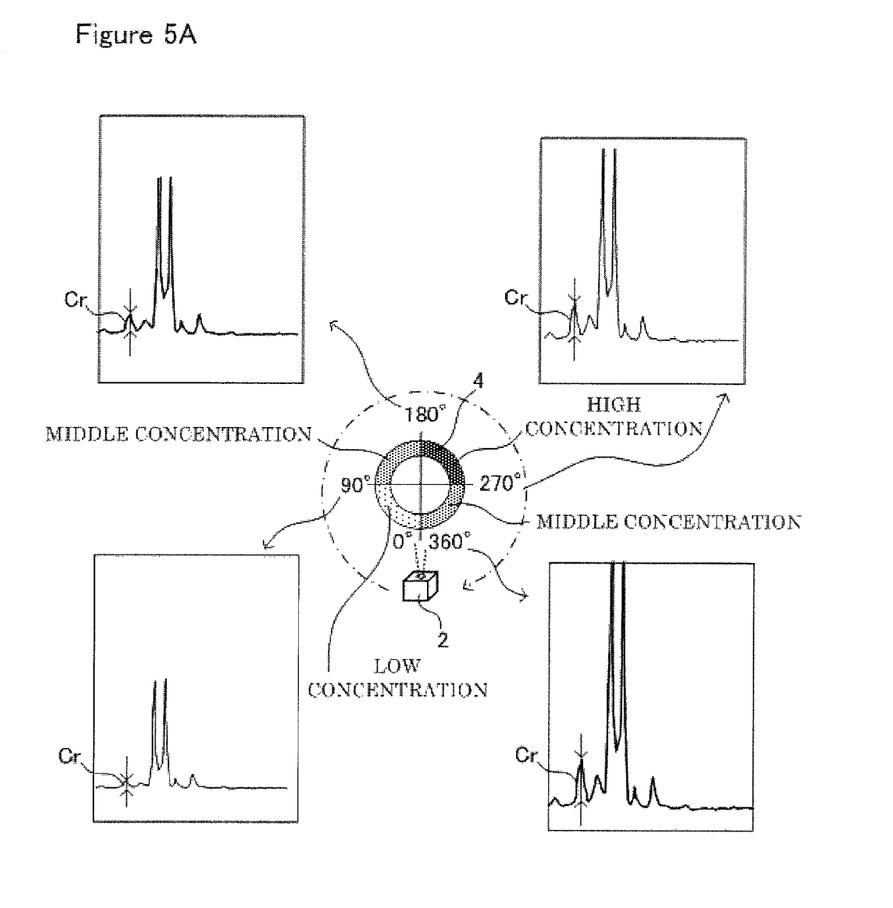
FIG. 5A is a diagram to show energy spectrums when the measurement section 2 has relatively moved to the positions of 90°, 180°, 270° and 360° in the detection step and the calculation step in the same method for determining the steel grade.
Figure 5B:
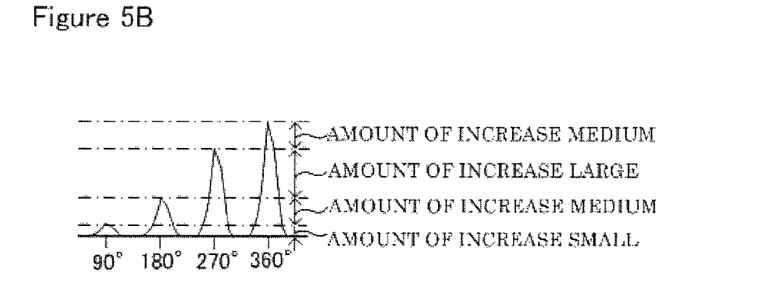
FIG. 5B is a diagram to show peaks of Cr in the energy spectrums at respective positions in FIG. 5A.

FIG. 5A shows energy spectrums when the measurement section 2 has relatively moved to the positions of 90°, 180°, 270° and 360°, and FIG. 5B shows peaks of Cr in the energy spectrums at respective positions.

The peak height of Cr increases according to the Cr concentrations at respective positions as the relative movement of the measurement section 2 proceeds. Therefore, the amount of increase from 0° to 90° is small, and the amount of increase from 180° to 270° is large. Thus, the amount of increase differs depending on the position in the pipe circumferential direction. Since the analysis value of Cr is calculated from the peak height of Cr when the time period necessary for analysis has elapsed (when the measurement section 2 has arrived at the position of 360°), the Cr concentration in the pipe circumferential direction is represented in an averaged manner.

Figure 6:
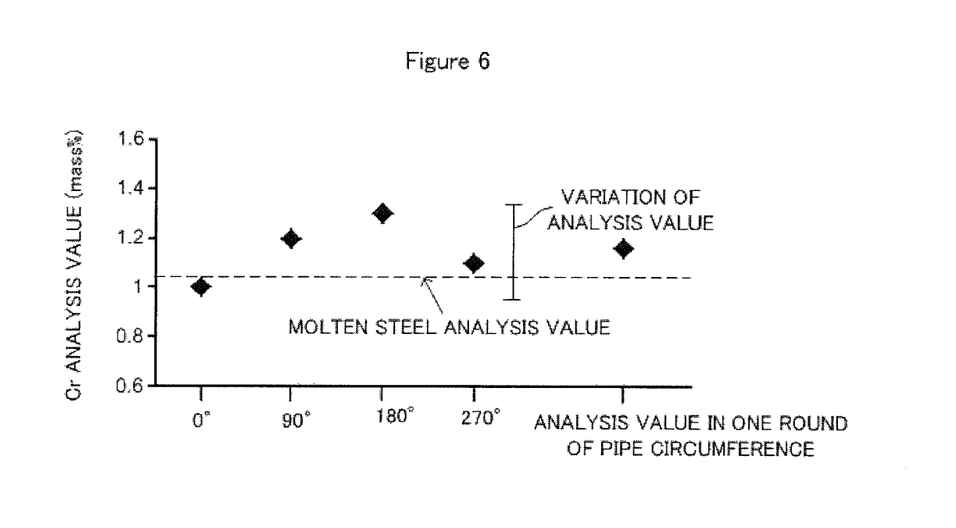
FIG. 6 is a diagram to show the analysis values of Cr in the same method for determining the steel grade.

FIG. 6 is a graph in which a graph of the analysis values of Cr at four positions in the circumferential direction of the steel pipe shown in FIG. 1 is added with analysis values obtained by fluorescent X-ray analysis for one round of pipe circumference as described above by using the same steel pipe. Thus, the analysis value in one round of pipe circumference is within the range of the variation of analysis values of Cr at four points in the pipe circumferential direction.

Upon end of the calculation step, the calculation control section 3 determines the steel grade of the steel pipe 4 from the calculated composition (determination step).

In steel grade determination, it may be determined that to which steel grade the steel pipe 4 belongs, or that whether the steel pipe 4 is a steel pipe of a predetermined steel grade, or a steel material of other than the predetermined steel grade. Further, it may also be arranged to only output the composition of the steel pipe 4.

Figure 7:
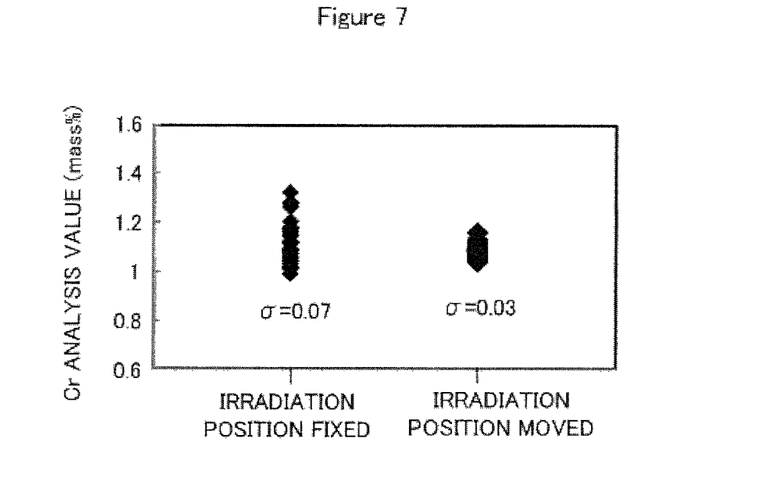
FIG. 7 is a diagram to show analysis values by a conventional method in which fluorescent X-ray analysis is performed with the X-ray irradiation position being fixed, and analysis values by the method of the present embodiment in which fluorescent X-ray analysis is performed with the X-ray irradiation position being moved by one round in the pipe circumferential direction.

FIG. 7 shows analysis values by a conventional method in which fluorescent X-ray analysis is performed with the X-ray irradiation position being fixed, and analysis values by the method of the present embodiment in which fluorescent X-ray analysis is performed with the X-ray irradiation position being moved by one round in the pipe circumferential direction. In each method, 20 steel pipes which were manufactured from the same molten steel were analyzed once for each. The 20 steel pipes analyzed by the conventional method and the 20 steel pipes analyzed by the method of the present embodiment are the same.

While the standard deviation of the variation of analysis values when 20 steel pipes were subjected to fluorescent X-ray analysis was 0.07 mass % in a conventional method, that was 0.03 mass % in the method of the present embodiment, and thus the method of the present embodiment shows a higher accuracy.

According to the present embodiment, since the steel material is irradiated with X-rays and the fluorescent X-rays radiated from the steel pipe 4 are detected while the measurement section 2 is relatively moved along the outer peripheral surface of the steel pipe 4 with respect to the steel pipe 4, the compositions of the portion irradiated with X-rays are calculated in an averaged manner. Therefore, the variation of analysis values decreases, thereby allowing accurate steel grade determination to be performed. In particular, in a steel pipe which contains any of elements of Cr, Cu, and Ni in an amount not less than 0.3 mass %, the variation of analysis values will decrease, thereby allowing accurate steel grade determination to be performed.

Moreover, since a fluorescent X-ray analyzer 1 which is the same as conventional one can be used for the fluorescent X-ray analyzer in the present embodiment, and the time period necessary for analysis may also be the same as in the past, it is possible to easily perform a steel grade determination.

That is, according to the present embodiment, even though it is possible to arrange for that the same equipment as in conventional fluorescent X-ray analysis is used, and the time period necessary for analysis is the same as in the past, the effect of surface oxide scale can be reduced, thereby allowing accurate analysis to be easily performed. This analysis allows the steel grade determination of steel pipe 4 to be accurately and easily performed.

Further, since the fluorescent X-ray analysis is performed not on the end face, but on the outer peripheral surface of the steel pipe 4, it is easier to automate the fluorescent X-ray analysis in the manufacturing line.

(Second Embodiment)

The present embodiment is different from the first embodiment in the method of the determination step.

The present inventors have found that in a steel material containing Cr and Ni such as a stainless steel, Cr and Ni are unevenly distributed in a surface oxide scale in a similar manner. Accordingly, in the determination step of the present embodiment, steel grade determination is performed not only according to the composition of steel material, but also according to the ratio between Cr and Ni concentrations.

Figure 8A:
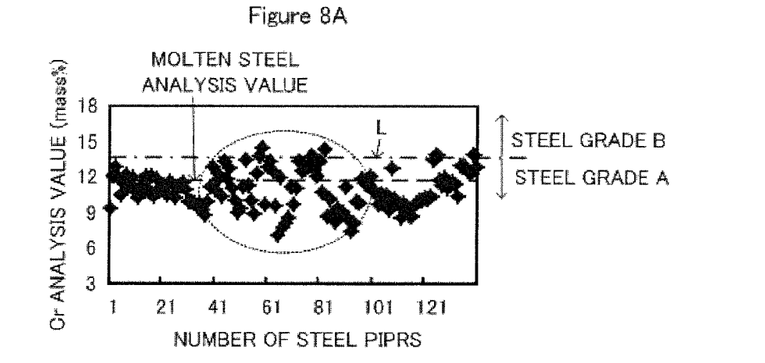
FIG. 8A is a diagram to show analysis values of Cr.
Figure 8B:
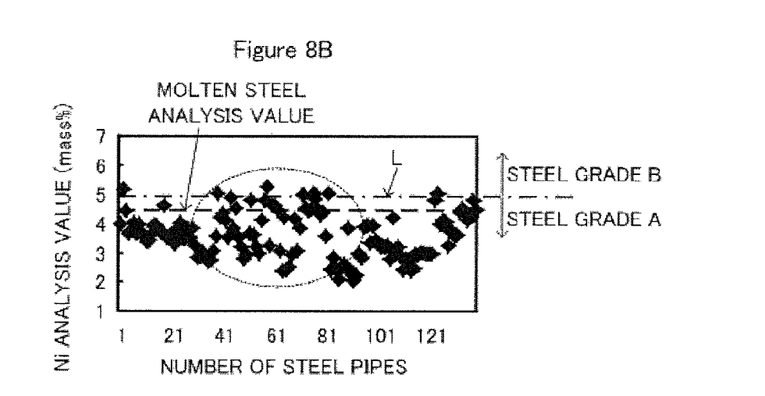
FIG. 8B is a diagram to show analysis values of Ni.
Figure 8C:
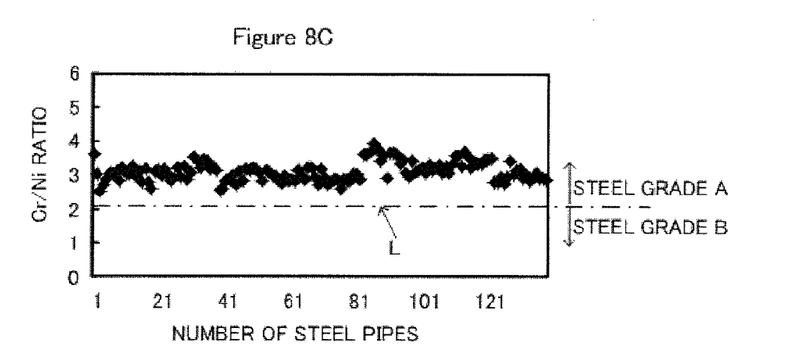
FIG. 8C is a diagram to show the ratio between Cr and Ni concentrations.

FIG. 8 show results of analysis of a steel pipe in a manufacturing line by the fluorescent X-ray analysis relating to the first embodiment, in which FIG. 8A shows analysis values of Cr, FIG. 8B shows analysis values of Ni, and FIG. 8C shows the ratio between Cr and Ni concentrations. The dashed line L in each figure is a reference line by which it is determined whether the steel grade of the steel pipe analyzed is steel grade A (Cr: 11.90 mass %, Ni: 4.50 mass %) or steel grade B (Cr: 18.00 mass %, Ni: 9.00 mass %).

While the steel pipe subjected to analysis is a steel pipe which has been determined to be of steel grade A in advance, since the variation of analysis values of Cr is large in the range surrounded by a dotted line in FIG. 8A, and some of analysis values of Cr exceed the reference line, those steel pipes are erroneously determined to be of steel grade B. Similarly, since the variation of analysis values of Ni is large in the range surrounded by the dotted line in FIG. 8B and some of analysis values of Ni exceed the reference line, those steel pipes are erroneously determined to be of steel grade B.

However, as shown in FIG. 8C, the Cr/Ni ratio has a small variation, and the Cr/Ni ratio is above a reference line in all the steel pipes so that all the steel pipes are determined to be of steel grade A.

In this way, even when the determination according to composition may result in an erroneous determination, there may be a case where the determination according to Cr/Ni ratio results in a right determination.

Therefore, in the present embodiment, when a steel material contains Cr and Ni, steel grade determination is performed by both the determination according to the composition of the steel material, and the determination according to Cr/Ni ratio. The steel grade determination is, for example, performed as follows. In this occasion, the range of Cr/Ni ratio is determined in advance for each steel grade, for example, from actual results.

<When Determining to which Steel Grade the Targeted Steel Material Belongs>

When a targeted steel material is determined to be of steel grade C by the determination according to composition, and the Cr/Ni ratio falls into the range of Cr/Ni of steel grade C, that is, the determination result according to composition agrees with the determination according to Cr/Ni ratio, the steel grade is determined to be steel grade C following the determination according to composition.

On the other hand, while the targeted steel material is determined to be of steel grade C by the determination according to composition, if the Cr/Ni ratio does not fall into the range of Cr/Ni ratio of steel grade C, that is, if the determination result according to composition does not agree with the determination according to Cr/Ni ratio, fluorescent X-ray analysis is performed again on a portion without surface oxide scale of the targeted steel material and according to the composition, steel grade determination is performed.

<When Determining Whether the Targeted Steel Material is a Steel Material of a Predetermined Steel Grade D or a Steel Material Other than the Predetermined Steel Grade D>

When a steel material is determined to be of steel grade D by the determination according to composition, and Cr/Ni ratio falls into the range of the Cr/Ni ratio of steel grade D, that is, the determination result according to composition agrees with the determination according to Cr/Ni ratio, the steel grade is determined to be steel grade D following the determination according to composition and the determination according to Cr/Ni ratio.

On the other hand, even though the steel grade is determined to be steel grade D by the determination according to composition, if Cr/Ni ratio does not fall into the range of Cr/Ni ratio of steel grade D, that is, the determination result according to composition does not agree with the determination according to Cr/Ni ratio, the steel grade is determined to be other than steel grade D following the determination result according to Cr/Ni ratio since the determination according to Cr/Ni ratio is more accurate than the determination according to composition. Further, when even though the steel material is determined not to be of steel grade D by the determination according to composition, Cr/Ni ratio falls into the range of Cr/Ni ratio of steel grade D, that is, when the determination result according to composition does not agree with the determination according to Cr/Ni ratio, the steel grade is determined to be steel grade D following the determination result according to Cr/Ni ratio rather than the determination according to composition, since the determination according to Cr/Ni ratio is more accurate than the determination according to composition.

Thus, not by performing steel grade determination only according to the composition of steel material, but by performing steel grade determination by both the determination according to composition and the determination according to the ratio between Cr and Ni concentrations, it is possible to perform more accurate determination.

It is noted that the present invention will not be limited to the configuration of the above embodiments, various variations are possible within a range not changing the spirit of the invention.

<Reference Signs List>
2 Measurement section
21 Irradiation section
22 Detection section
4 Steel tube (steel material)

The invention claimed is:

1. A method of steel grade determination for a steel material having a substantially circular cross-section and a surface layer oxide scale on an outer peripheral surface thereof, by means of a fluorescent X-ray analysis method in a manufacturing line of the steel material, the method of steel grade determination for a steel material having the substantially circular cross-section comprising:
   a detection step in which while a measurement section including an irradiation section for performing X-ray irradiation and a detection section for detecting fluorescent X-rays is relatively moved along an outer peripheral surface of the steel material with respect to the steel material for a predetermined time period necessary for analysis, the steel material is irradiated with X-rays from the irradiation section, and fluorescent X-rays radiated from the steel material are continuously detected by the detection section while the measurement section is relatively moved;
   a calculation step of calculating an averaged composition of all of portions of the steel material in which fluorescent X-rays are detected, based on an energy spectrum obtained from a number of fluorescent X-ray counts at each energy level of the fluorescent X-rays detected while the measurement section is relatively moved in the detection step; and
   a determination step of determining a steel grade of the steel material according to the composition calculated in the calculation step.

2. The method of steel grade determination for a steel material having a substantially circular cross-section according to claim 1, wherein
   the steel material contains not less than 9 mass % of Cr and contains Ni, and in the determination step, a steel grade of the steel material is determined according to the composition and according to a ratio between Cr and Ni concentrations in the composition.

3. The method of steel grade determination for a steel material having a substantially circular cross-section according to claim 1, wherein
   a distance of the relative movement of the measurement section along an outer peripheral surface of the steel material with respect to the steel material is not less than ½ round around the steel material and not more than 2 rounds around the steel material.

* * * * *